United States Patent
Salvemini et al.

(10) Patent No.: US 12,397,010 B2
(45) Date of Patent: Aug. 26, 2025

(54) TREATMENT OF CHRONIC HEADACHES

(71) Applicants: Saint Louis University, St. Louis, MO (US); University of Maryland, Baltimore, Baltimore, MD (US)

(72) Inventors: Daniela Salvemini, Chesterfield, MO (US); Simon Akerman, Baltimore, MD (US); Marcela Romero-Reyes, Baltimore, MD (US)

(73) Assignees: Saint Louis University, St. Louis, MO (US); University of Maryland, Baltimore, Baltimore, MD (US)

( * ) Notice: Subject to any disclaimer, the term of this patent is extended or adjusted under 35 U.S.C. 154(b) by 809 days.

(21) Appl. No.: 17/431,318

(22) PCT Filed: Feb. 14, 2020

(86) PCT No.: PCT/US2020/018410
§ 371 (c)(1),
(2) Date: Aug. 16, 2021

(87) PCT Pub. No.: WO2020/168274
PCT Pub. Date: Aug. 20, 2020

(65) Prior Publication Data
US 2022/0117985 A1   Apr. 21, 2022

Related U.S. Application Data

(60) Provisional application No. 62/806,200, filed on Feb. 15, 2019.

(51) Int. Cl.
*A61K 31/708* (2006.01)
*A61P 25/06* (2006.01)

(52) U.S. Cl.
CPC ............ *A61K 31/708* (2013.01); *A61P 25/06* (2018.01)

(58) Field of Classification Search
CPC ........ A61K 31/52; A61K 25/06; A61K 29/00; C07C 13/38; C07D 473/00
USPC .......................................................... 514/46
See application file for complete search history.

(56) References Cited

U.S. PATENT DOCUMENTS

| | | |
|---|---|---|
| 8,518,957 B2 | 8/2013 | Jacobson et al. |
| 8,735,407 B2 | 5/2014 | Jacobson et al. |
| 8,796,291 B2 | 8/2014 | Jacobson et al. |
| 8,916,570 B2 | 12/2014 | Jacobson et al. |
| 9,123,131 B2 | 9/2015 | Teo et al. |
| 9,181,253 B2 | 11/2015 | Jacobson et al. |
| 9,963,450 B2 | 5/2018 | Jacobson et al. |
| 10,577,368 B2 * | 3/2020 | Jacobson ............. C07D 473/00 |
| 2015/0087613 A1 | 3/2015 | Salvemini |
| 2017/0002007 A1 | 1/2017 | Jacobson et al. |

FOREIGN PATENT DOCUMENTS

| | | | | |
|---|---|---|---|---|
| WO | WO 2007/064795 A2 * | 6/2007 | ............. | A61K 31/70 |
| WO | WO 2015/080940 A1 * | 6/2015 | ........... | C07D 473/00 |

OTHER PUBLICATIONS

Coppi et al., Adenosine A3 receptor activation inhibits pronociceptive N-type Ca2+ currents and cell excitability in dorsal root ganglion neurons; 2019, Pain, vol. 160, No. 5, pp. 1103-1118.

Tosh et al., In Vivo Phenotypic Screening for Treating Chronic Neuropathic Pain: Modification of C2-Arylethynyl Group of Conformationally Constrained A3 Adenosine Receptor Agonists; Journal of Medicinal Chemistry, 2014, vol. 57, pp. 9901-9914.

Tosh et al., Efficient, large-scale synthesis and preclinical studies of MRS5698, a highly selective A3 adenosine receptor agonist that protects against chronic neuropathic pain; 2015, Purinergic Signalling, vol. 11, pp. 371-387.

Tosh et al., Structure-Based Design, Synthesis by Click Chemistry and in Vivo Activity of Highly Selective A3 Adenosine Receptor Agonists; 2015, Medchemcomm., vol. 6, pp. 555-23.

Tosh et al., Rigidified A3 Adenosine Receptor Agonists: 1-Deazaadenine Modification Maintains High in Vivo Efficacy; ACS Medicinal Chemistry Letters; 2015, vol. 6, pp. 804-808.

Tosh et al., Purine (N)-Methanocarba Nucleoside Derivatives Lacking an Exocyclic Amine as Selective A3 Adenosine Receptor Agonists; Journal of Medicinal Chemistry, 2016, vol. 59, pp. 3249-3263.

\* cited by examiner

*Primary Examiner* — Ganapathy Krishnan
(74) *Attorney, Agent, or Firm* — Sandberg Phoenix & von Gontard, PC; Steven T. Kazmierski

(57) ABSTRACT

Disclosed herein are methods and compositions for the treatment and prevention of migraine, migraine-like headaches such as post-traumatic headache, and other related headaches by administering to a subject in need thereof a selective agonist for the human adenosine A3 receptor (A3AR) subtype.

19 Claims, 1 Drawing Sheet

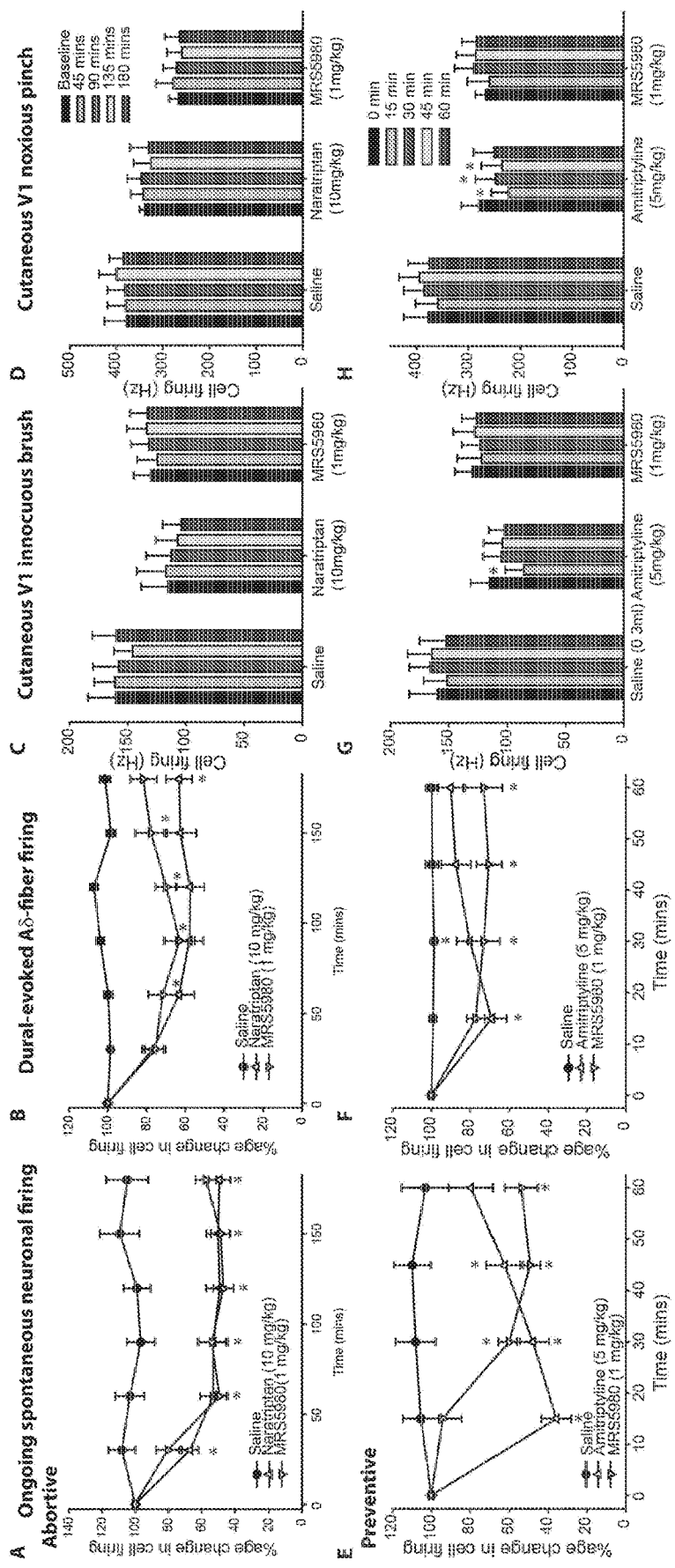

TREATMENT OF CHRONIC HEADACHES

RELATED APPLICATION INFORMATION

This application is a U.S. national stage application of International Patent Application No. PCT/US2020/018410 filed Feb. 14, 2020, which claims the benefit of U.S. Provisional Application No. 62/806,200 filed Feb. 15, 2019, each of which is entirely incorporated herein by reference for all purposes.

BACKGROUND OF THE DISCLOSURE

The present disclosure relates to the field of medicine. Specifically, the present disclosure is directed to the use of a drug that is a selective agonist for the human adenosine A3 receptor (A3AR) subtype for the treatment and prevention of migraine, migraine-like headaches such as post-traumatic (post-concussive) headache, and other related headaches thought to be mediated by activation and/or sensitization of the pain-responsive sensory neurons that innervate the dura mater and its vasculature.

Migraine, a chronically episodic moderate-severe headache, predominantly felt on one side of the head, is one of the most common and disabling neurological disorders. It affects 15-18% of people worldwide each year. Women are more likely to be affected, with a 3:1 female/male prevalence in adults. In 2004 migraine was thought to cost the USA economy at least $20 billion a year. The two most common types are migraine with aura and migraine without aura, but based upon the International Classification for Headache Disorders (ICHD-III) the headache is classified as similar or identical in both types. Migraine is a chronic condition, with periodic headaches occurring for decades or throughout a life-time.

Post-traumatic headache (PTH) is the most common symptom after a traumatic brain injury (TBI). PTH affects up to 1.7 million civilians in the USA each year; 75% of these cases present after mild TBI. A mild TBI is synonymous with a concussion, and the post-injury headache and other symptoms are also called the concussion syndrome. Mild TBI occurs with a closed head injury, consciousness is either not interrupted or lost for no more than 30 minutes, the patient's Glasgow Coma Scale rating is near normal (13-15), and post injury amnesia is absent or extends for no more than one day. Neuroimaging studies detect subtle signs of brain damage in only a minority of cases. The headaches can be episodic and frequent (e.g., daily, 2-3 times per week, etc.) or they be nearly constant. In most patients, PTH resolves over a period of weeks to months, but in some patients the headaches persist for years.

Trigeminal autonomic cephalalgias (TACs) are another subclass of primary headaches. The most common of which is cluster headache. These are much rarer than migraine, cluster headache is thought to affect 0.1% of the population. However, the pain in these headaches is rated severe or very severe, and is strictly unilateral, generally perceived intracranially in or around the orbital region. These headaches are also defined by their association with prominent cranial parasympathetic autonomic features, lateralized to the headache side, such as lacrimation, nasal congestion, and rhinorrhea (based on the ICHD-III). These headaches can also become chronic.

Migraine, and migraine-like headaches such as PTH, are currently treated acutely to abort the ongoing headache with drugs from the triptan class (e.g. sumatriptan), non-steroidal anti-inflammatory drugs, and opioids. For prevention to reduce headache frequency and severity over time, they are treated with drugs developed for other indications, including tricyclic antidepressants (e.g., amitriptyline), specific antiepileptics (valproate and topiramate), and 0-blockers (propranolol and metoprolol). Most recently a new class of drug has been approved, which are antibodies directed at the calcitonin gene-related peptide (CGRP) signaling pathway, for use in prevention only. No new drugs have been developed for TACs. For cluster headaches first choice options to treat acutely are with oxygen and subcutaneous sumatriptan. There is also evidence of efficacy for intranasal sumatriptan and zolmitriptan. For prevention verapamil, lithium and steroids are recommended. For other TACs there are no acute treatments due to the short duration of these attacks. Preventive treatments include indomethacin, lamotrigine, topiramate and gabapentin.

While there have been significant advances in treatments for migraine and migraine-like headaches, our ability to treat these conditions is still very limited. There continue to be millions of individuals for whom currently available headache therapies are only partially effective or ineffective, and many of these treatments are poorly tolerated, with many adverse side-effects. Additionally, when acute treatments (e.g. triptans, NSAIDs, opioids) are overused they can result in a rebound headache, termed medication overuse headache, this can be a new headache, or worsening of their pre-existing headache. There is therefore a critical need to identify novel targets for the treatment of migraine, migraine-like headaches such as PTH, and other headache disorders, such as TACs.

Migraine, migraine-like headaches such as PTH, as well as other related headaches are believed to involve activation and sensitization of the trigeminal (meningeal) nociceptors (i.e., pain-responsive sensory neurons) that innervate the dura mater and its vasculature. Drugs that are known to abort migraine headaches, and also decrease the frequency and severity of headaches when dosed chronically are known to inhibit the discharge of meningeal nociceptors in animal models. We have discovered that drugs that are selective agonists for the adenosine A3 receptor (A3AR) subtype also inhibit the discharge of these trigeminal neurons. It thus follows that A3AR agonists will be treatments for migraine, migraine-like headaches such as PTH, as well as other related headaches. Our observations thus indicate that A3AR agonists will act to abort an ongoing headache and also to decrease the frequency and severity of headaches when dosed chronically.

A3AR agonists are already under development for the treatment of chronic inflammatory and neuropathic pain conditions. In animal models, A3AR agonists are well tolerated, have a good therapeutic index, and produce potent and persistent pain relief in diverse rodent models of pain. Tolerance to their analgesic action does not occur and their analgesic effect is independent of any action at opioid or cannabinoid receptors.

It is known that in the brain the purine nucleoside, adenosine, is a major neuroprotective molecule, and that nerve cells, glia and other cell types express receptors on their membranes that have adenosine as their natural ligand. There are known to be four G-protein-coupled receptor subtypes for adenosine: $A_1AR$, $A_{2A}AR$, $A_{2B}AR$, and $A_3AR$ (A3AR). Drug-like molecules are known that have selectivity for binding to each of the four subtypes. In particular, highly-selective (greater than 10,000-fold relative to each of the other three subtypes) agonists for the A3AR are available. Drugs that selectively activate the A3AR are advantageous because they avoid the cardiovascular, renal and immunological side-effects that are produced by activation of the other three receptor subtypes.

BRIEF DESCRIPTION OF THE DISCLOSURE

In accordance with the present disclosure, there is provided methods for treating and preventing migraine, migraine-like headaches such as post-traumatic headache, and other related headaches by administering a selective agonist for the human adenosine A3 receptor (A3AR) subtype to a patient in need thereof.

Also disclosed are methods for prophylactically treating headaches by administering a selective agonist for the human adenosine A3 receptor (A3AR) subtype to a patient in need thereof.

It is contemplated that any method or composition described herein can be implemented with respect to any other method or composition described herein.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 1A-1H depict a preclinical model of migraine manipulates the pain responsive sensory neurons that innervate the dura mater and its associated blood vessels. The cell bodies of these sensory neurons reside in the trigeminal ganglia. Measuring dural-responsive trigeminal neuronal responses in animals has proven to be extremely predictive of therapeutic efficacy for abortive migraine treatments, such as triptans, and it also translates to migraine preventives. Here we show in vivo electrophysiological recordings in a rat from single unit trigeminal neurons that innervate the dural vasculature. The discharge of such neurons has previously been demonstrated to evoke headache in humans. Intravenous administration of the migraine abortive, naratriptan (FIGS. 1A-1D) and the migraine preventive, amitriptyline (FIGS. 1E-1H), inhibited ongoing neuronal firing (FIGS. 1A & 1E) and the response to pain-producing stimulation of the dura mater (FIGS. 1B & 1F) of central trigeminal neurons. The selective A3AR agonist, MRS5980, was equally efficacious in inhibiting neuronal responses. In the same neurons, naratriptan and MRS5980 had no effect on normal cutaneous facial noxious and innocuous somatosensory responses. Amitriptyline, however did affect this normal somatosensory processing. * P<0.05 vs. baseline. These data indicate that activation of the A3AR only affected pathological intracranial pain, and did not affect normal extracranial somatosensory processing, and therefore A3AR activation provides a novel and effective target for the treatment of migraine, migraine-like headaches, and other related headaches.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

As used herein, "a subject in need thereof" refers to a subject susceptible to or at risk of a specified disease, disorder, or condition. More particularly, in the present disclosure the methods of treating and preventing migraine, migraine-like headaches such as post-traumatic headache, and other related headaches is to be used with a subset of subjects who are susceptible to or at elevated risk for experiencing migraine, migraine-like headaches such as post-traumatic headache, and other related headaches. Subjects may be susceptible to or at elevated risk for migraine, migraine-like headaches such as post-traumatic headache, and other related headaches due to family history, age, environment, and/or lifestyle. The methods for prophylactically treating headaches to be used with a subset of subjects who are susceptible to or at elevated risk for experiencing migraine, migraine-like headaches such as post-traumatic headache, and other related headaches.

Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

As used herein, "susceptible" and "at risk" refer to having little resistance to a certain disease, disorder or condition, including being genetically predisposed, having a family history of, and/or having symptoms of the disease, disorder or condition.

In one aspect, the present disclosure is directed to methods for treating and preventing migraine, migraine-like headaches such as post-traumatic headache, and other related headaches by administering a selective agonist for the adenosine A3 human receptor subtype to a patient in need thereof. The present disclosure is also directed to prophylactically treating migraine, migraine-like headaches such as post-traumatic headache, and other related headaches by administering a selective agonist for the adenosine A3 human receptor subtype to a patient in need thereof.

It can be confirmed that a compound is a selective A3AR agonist using known methods, including competitive radioimmunoassays and assays of forskolin-stimulated cyclic adenosine monophosphate (cAMP) production in human A3AR transfected CHO cells or HEK cells. "Selective" is herein defined as binding affinity (or cAMP production) for the human A3 receptor subtype that is at least 50-fold greater than the binding affinity (or cAMP production) for any of the other three human receptor subtypes. It is important to specify selectivity with respect to the human form of the A3AR because agonists are known to have significantly different binding affinities for A3AR's from other species.

Suitable selective agonists for the human A3AR may be chosen from, but not limited to, any of the following: (i) $N^6$-benzyladenosine-5'-N-methyluronamides such as $N^6$-(3-iodobenzyl)-adenosine-5'-N-methyluronamide (also known as IB-MECA), and 2-Chloro-$N^6$-(3-iodobenzyl)-adenosine-5'-N-methyluronamide (also known as 2-Cl-IB-MECA); (ii) (N)-methanocarba nucleosides such as (1R,2R,3S,4R)-4-(2-chloro-6-((3-chlorobenzyl)amino)-9H-purin-9-yl)-2,3-dihydroxy-N-methylbicyclo[3.1.0]hexane-1-carboxamide (also known as CF502, Can-Fite Biopharma, MA); (2S,3S,4R,5R)-3-amino-5-[6-(2,5-dichlorobenzylamino)purin-9- yl]-4-hydroxy-tetrahydrofuran-2-carboxylicacid methylamide (also known as CP-532,903); (1'S,2'R,3'S,4'R,5'S)-4-(2-chloro-6-(3-chlorobenzylamino)-9H-purin-9-yl)-2,3-dihydroxy-N-methylbicyclo[3.1.0]hexane-N-carboxamide (also known as MRS-3558); (1'R,2'R,3'S,4'R,5'S)-4-{2-chloro-6-[(3-iodophenylmethyl)amino]purin-9-yl-}-1-(methylaminocarbonyl)-bicyclo[3.1.0]hexane-2,3-diol (also known as MRS1898); and (iii) 2-Dialkynyl derivatives of (N)-methanocarba nucleosides, 2-(arylethynyl)adenine and N(6)-methyl or N(6)-(3-substituted-benzyl), N(6)-methyl 2-(halophenylethynyl) analogues, polyaromatic 2-ethynyl N(6)-3-chlorobenzyl analogues, such as 2-p-biphenylethynyl MRS5679 and fluorescent 1-pyrene adduct MRS5704, as well as MRS5678.

Particularly suitable highly-selective (<10,000-fold) A3AR agonists for use in the methods, include but are not limited to, the adenosine methanocarba derivatives described in Tosh et al. (2014; 2015a, 2015b, 2015c, and 2016). In certain embodiments, A3AR agonists may be selected from a compound described in any one of U.S. Pat. Nos. 9,963,450; 8,916,570; 8,735,407; 8,796,291; 9,181,253; and 9,123,131; and US Patent Application No. 20170002007, the compounds and chemical genuses of each of which are incorporated herein by reference. Also included herein by reference are the compounds and chemical genuses described in Publication No. WO2015080940. These compounds include but are not limited to those designated MRS5980, MRS7144, MRS7154, MRS7334, MRS7137, MRS7555, MRS7556, and MRS7557.

In certain embodiments, the A3AR agonist is a compound of the formula (I):

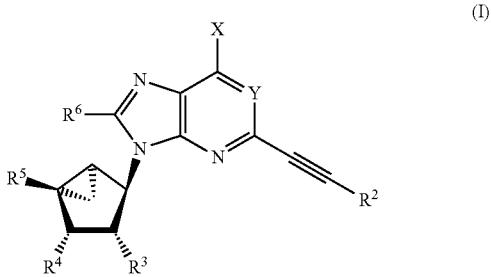

(I)

wherein: X is selected from $NHR^1$, $CH_3$, and $CH=C(R^a)(R^b)$ wherein $R^a$ and $R^b$ are independently selected from hydrogen, hydroxyl, $C_1$-$C_6$ alkyl, and $C_6$-$C_{14}$ aryl; Y is N or CH;

$R^1$ is selected from $C_1$-$C_6$ alkyl, $C_1$-$C_6$ alkoxy, hydroxyl, $C_3$-$C_8$ cycloalkyl, $C_6$-$C_{14}$ aryl $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkoxy, heterocyclyl $C_1$-$C_6$ alkyl, heterocyclyl, 4-[[[4-[[[(2-amino $C_1$-$C_6$ alkyl)amino]-carbonyl]-$C_1$-$C_6$ alkyl]anilino]carbonyl]$C_1$-$C_6$ alkyl] $C_6$-$C_{14}$ aryl, and $C_6$-$C_{14}$ aryl $C_3$-$C_8$ cycloalkyl, wherein the aryl or heterocyclyl portion of $R^1$ is optionally substituted with one or more substituents selected from halo, amino, hydroxyl, carboxy, alkoxycarbonyl, aminocarbonyl, alkylaminocarbonyl, dialkylaminocarbonyl, $C_1$-$C_6$ alkyl, $C_2$-$C_6$ alkenyl, $C_2$-$C_6$ alkynyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, carboxy $C_1$-$C_6$ alkyl, carboxy $C_2$-$C_6$ alkenyl, carboxy $C_2$-$C_6$ alkynyl, aminocarbonyl $C_1$-$C_6$ alkyl, aminocarbonyl $C_2$-$C_6$ alkenyl, aminocarbonyl $C_2$-$C_6$ alkynyl, and any combination thereof; and the alkyl or cycloalkyl portion of $R^1$ is optionally substituted with one or more substituents selected from halo, amino, alkyl, alkoxy, aryloxy, hydroxyalkyl, hydroxyalkenyl, hydroxyalkynyl, aminocarbonylalkoxy, and arylalkoxy, and any combination thereof;

$R^2$ is selected from $C_6$-$C_{12}$ aryl, $C_3$-$C_8$ cycloalkyl, heteroaryl, and metallocenyl, wherein the aryl group is substituted with one or more substituents selected from trifluoromethyl, hydroxyalkyl, alkoxy, sulfonyloxy, carboxyalkyl, sulfonyloxyalkyl, arylcarbonyl, and any combination thereof, wherein the heteroaryl group is optionally substituted with one or more substituents selected from halo, trifluoromethyl, amino, alkyl, hydroxyalkyl, aryl, benzo, alkoxy, hydroxyl, carboxyl, sulfonyloxy, carboxyalkyl, sulfonyloxyalkyl, alkylcarbonyl, arylcarbonyl, and any combination thereof;

$R^3$ and $R^4$ are independently selected from hydrogen, hydroxyl, amino, mercapto, ureido, $C_1$-$C_6$ alkyl carbonylamino, hydroxy $C_1$-$C_6$ alkyl, and hydrazinyl;

$R^5$ is selected from $C_1$-$C_3$ alkyl aminocarbonyl, di($C_1$-$C_3$ alkyl) aminocarbonyl, $C_1$-$C_3$ alkylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl; and $R^6$ is selected from hydrogen, $C_1$-$C_6$ alkyl, $C_2$-$C_6$ alkenyl, $C_2$-$C_6$ alkynyl, heteroaryl, and $C_1$-$C_6$ aminoalkyl;

or a pharmaceutically acceptable salt thereof.

In certain embodiments for a compound of formula (I), X is $NHR^1$, $R^1$ is $C_1$-$C_6$ alkyl, $R^2$ is $C_6$-$C_{10}$ aryl, wherein the aryl group is substituted with one or more substituents selected from halo, trifluoromethyl, hydroxyalkyl, alkoxy, and any combination thereof, or $R^2$ is heteroaryl, and the heteroaryl group is optionally substituted with one or more substituents selected from halo, hydroxy, and alkyl.

In certain embodiments for a compound of formula (I), when $R^1$ is methyl, $R^3$ and $R^4$ are both hydroxyl, $R^6$ is hydrogen, and $R^5$ is methylaminocarbonyl, $R^2$ is not 2-pyridyl or phenyl.

In certain embodiments for a compound of formula (I), when $R^1$ is methyl, $R^3$ and $R^4$ are both hydroxyl, $R^6$ is hydrogen, and $R^5$ is methylaminocarbonyl, $R^2$ is not 2-pyridyl.

In certain embodiments for a compound of formula (I), $R^6$ is hydrogen.

In certain embodiments for a compound of formula (I), Y is N.

In certain embodiments for a compound of formula (I), $R^5$ is selected from $C_1$-$C_3$ alkyl aminocarbonyl or di($C_1$-$C_3$ alkyl) aminocarbonyl.

In certain embodiments for a compound of formula (I), $R^3$ and $R^4$ are both hydroxyl.

In certain embodiments for a compound of formula (I), X is $NHR^1$. In a preferred embodiment, $R^1$ is $C_1$-$C_6$ alkyl.

In certain embodiments for a compound of formula (I), $R^2$ is $C_6$-$C_{10}$ aryl, wherein the aryl group is substituted with one or more substituents selected from halo, trifluoromethyl, hydroxyalkyl, alkoxy, and any combination thereof.

In certain embodiments for a compound of formula (I), $R^2$ is heteroaryl, and the heteroaryl group is optionally substituted with one or more substituents selected from hydroxy, halo and alkyl.

In certain embodiments, the compound is selected from:
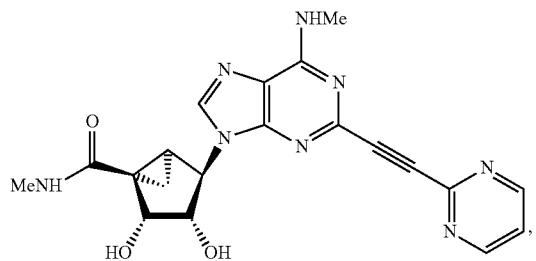
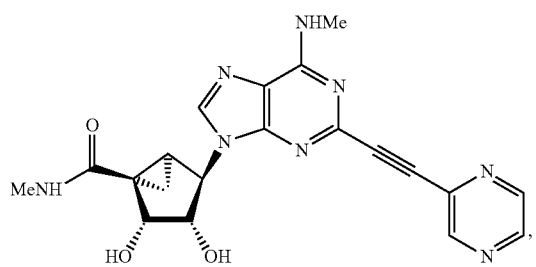
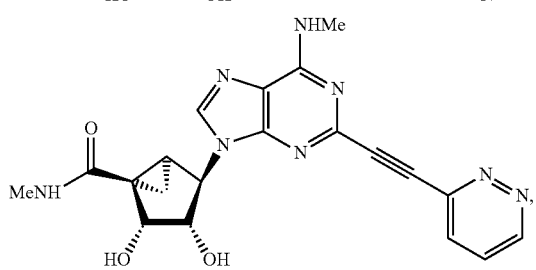
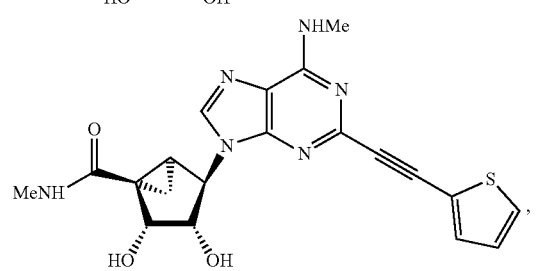
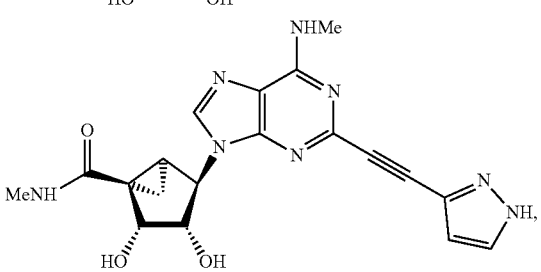
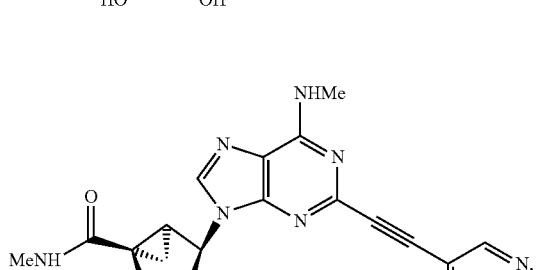
-continued
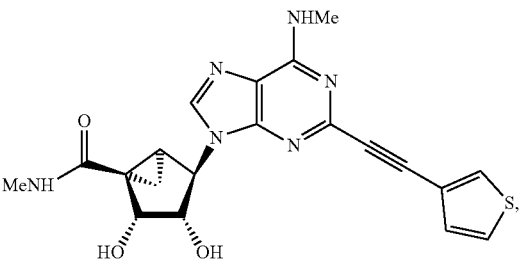
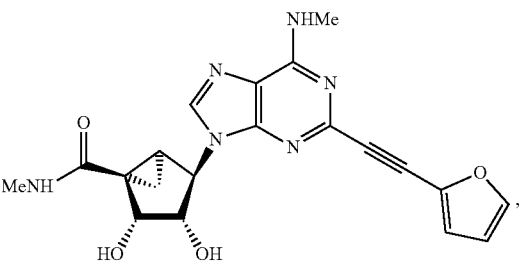
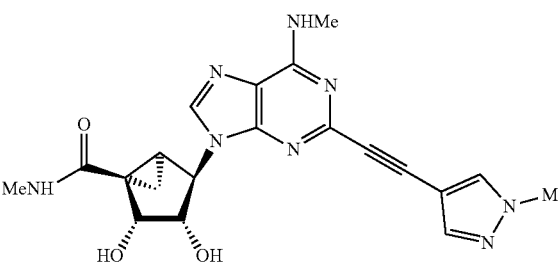
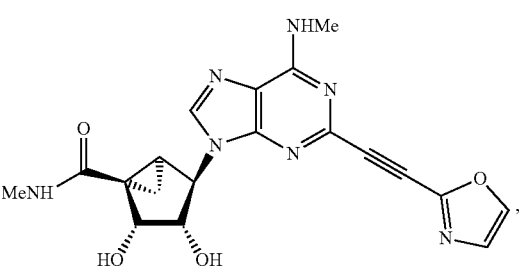
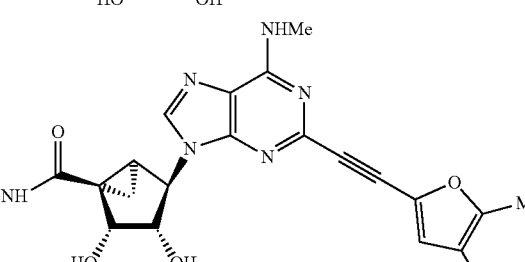
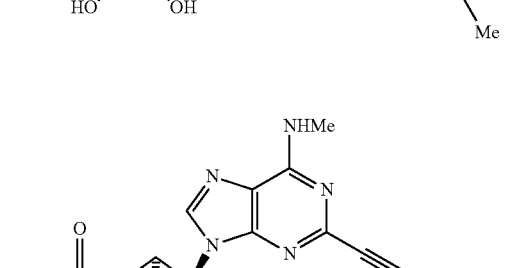

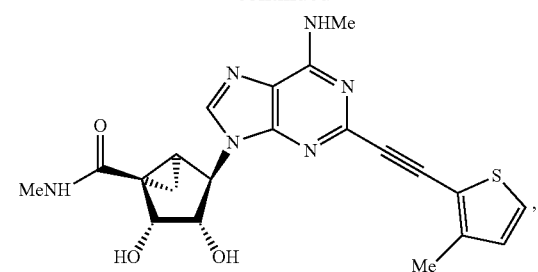
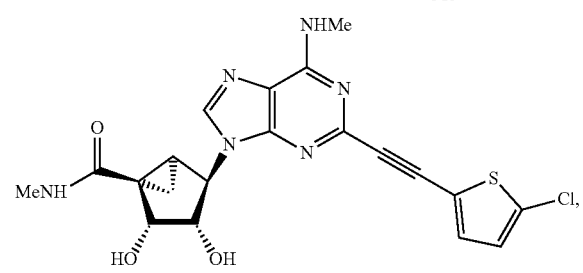
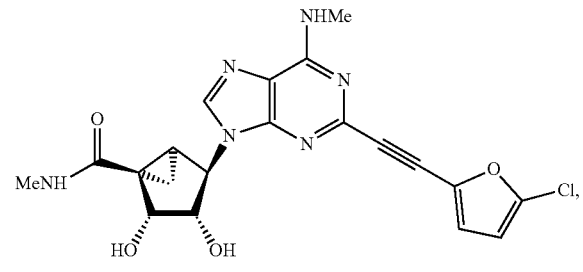
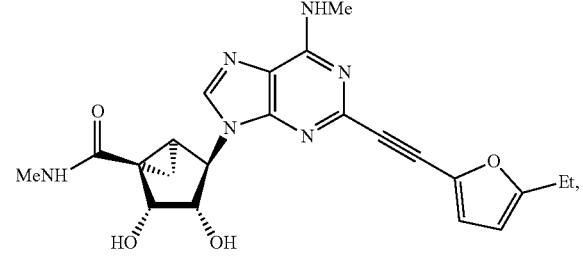
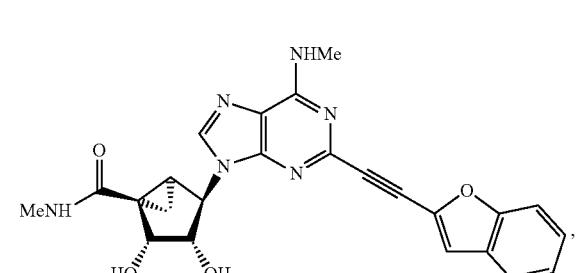
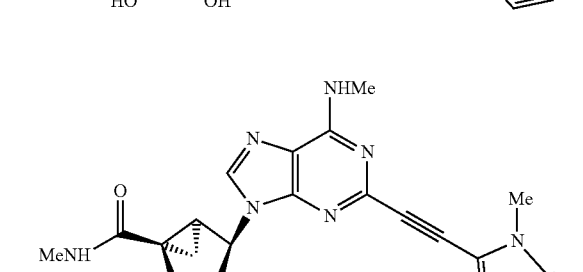
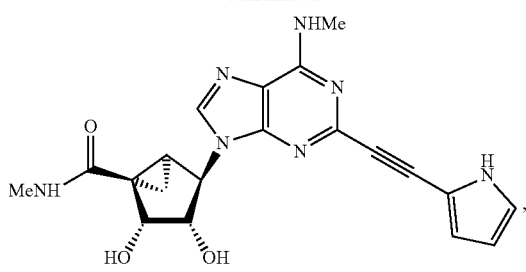
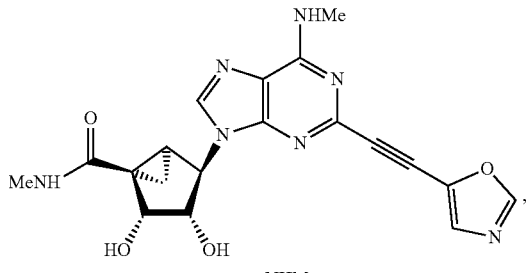
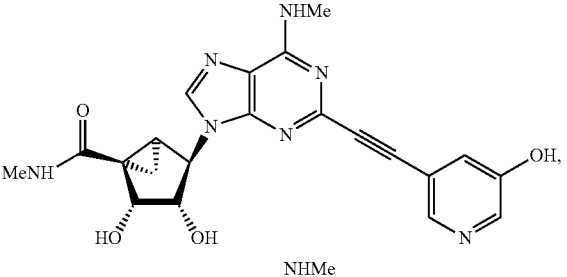
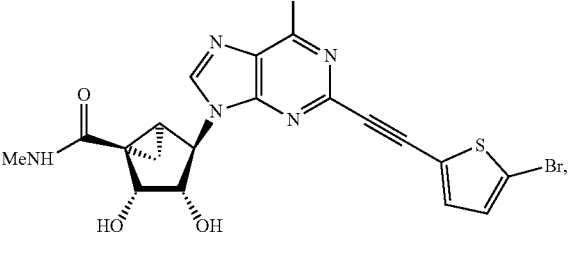
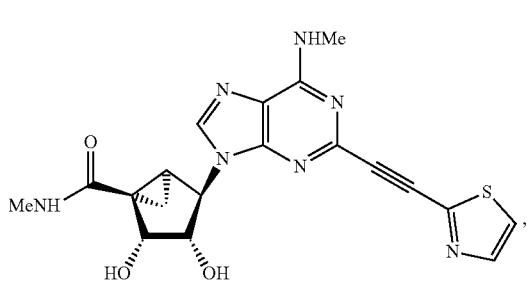
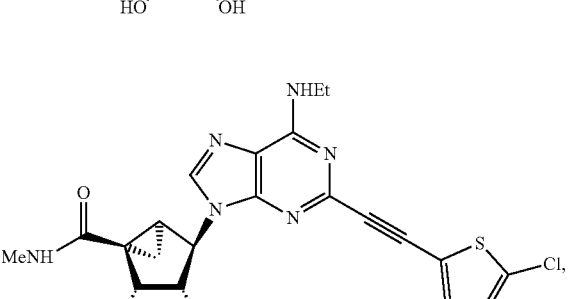

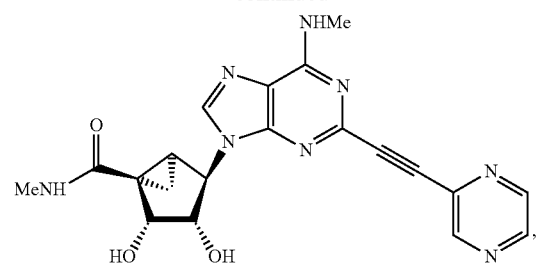
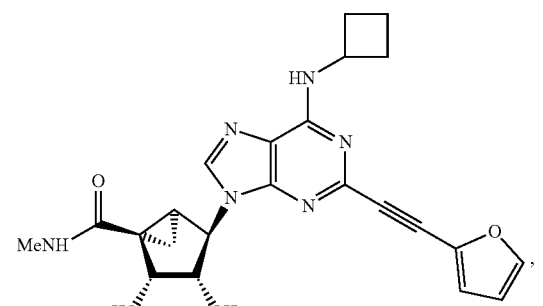
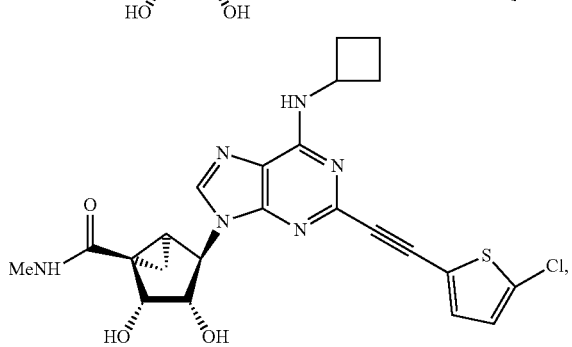
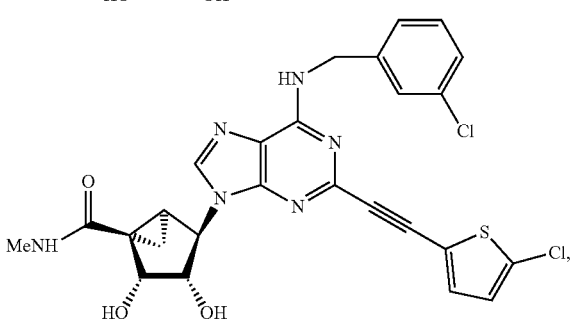
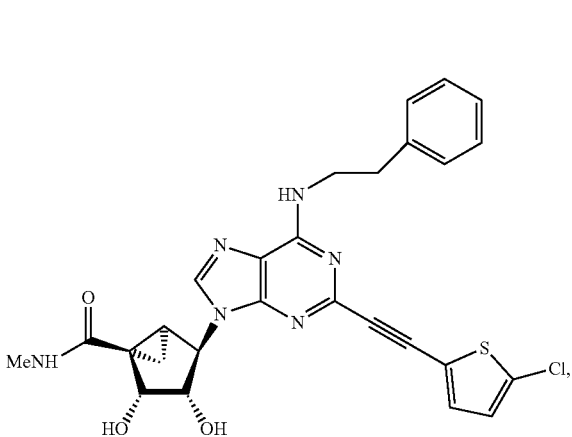
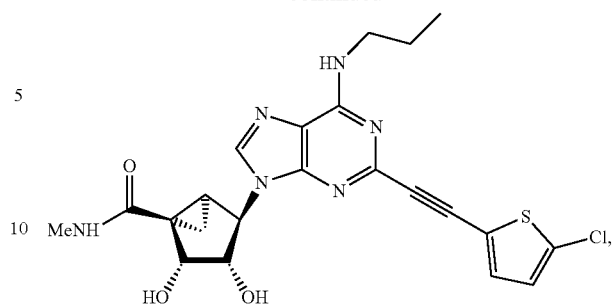
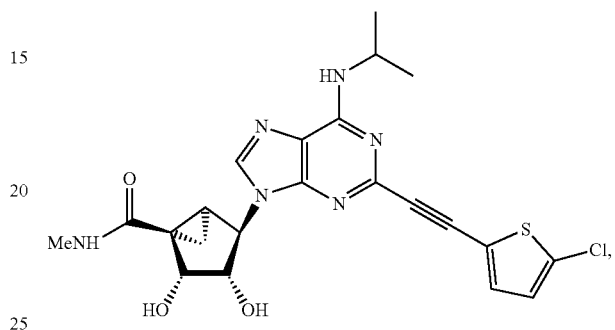
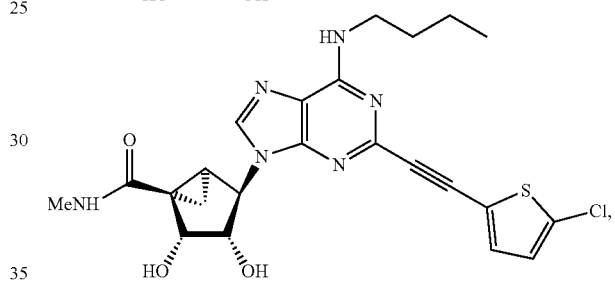
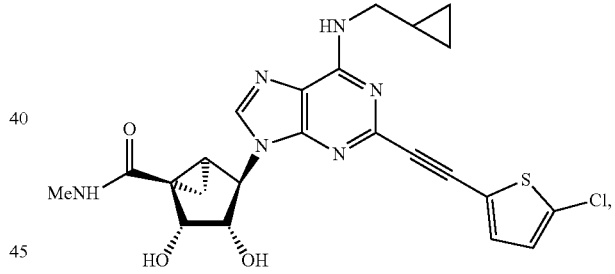
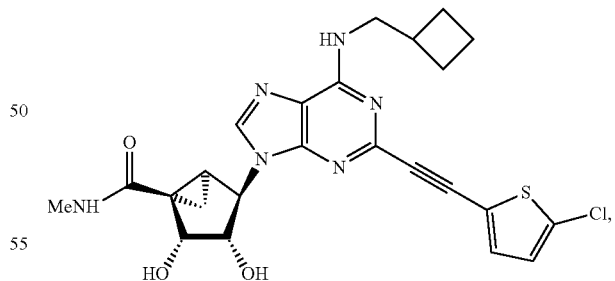
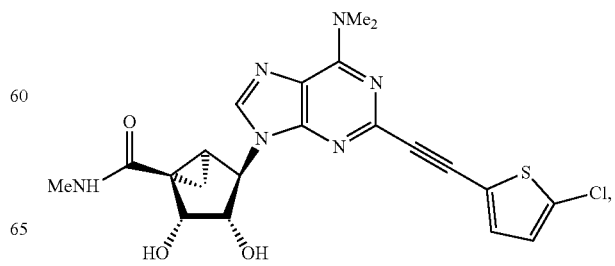

-continued

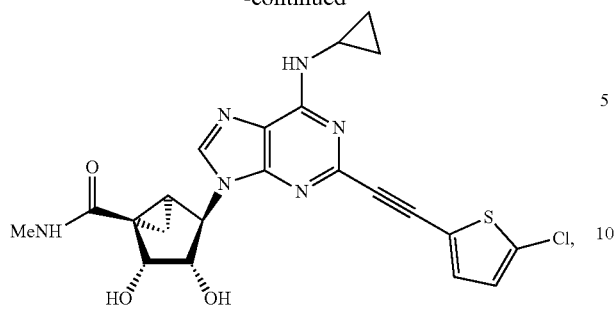

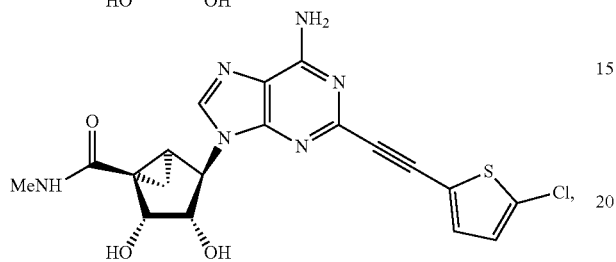

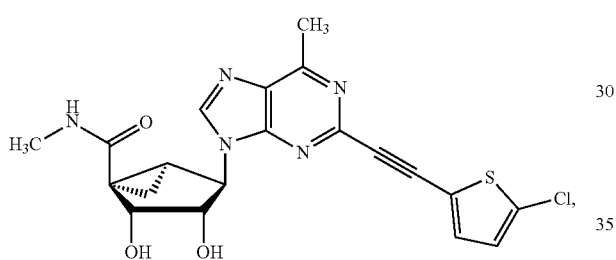

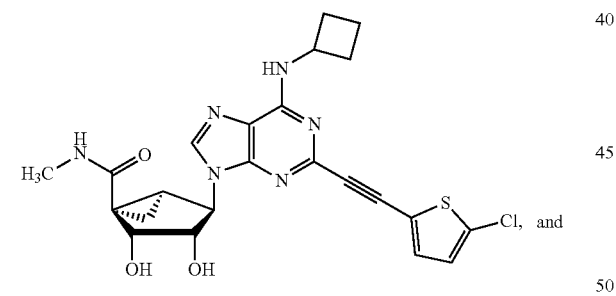

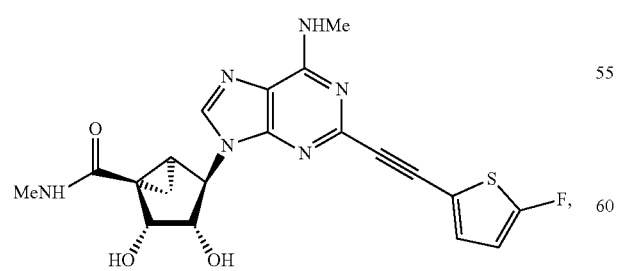

and a salt of any one thereof.

In certain embodiments, the A3AR agonist is a compound of the formula (II):

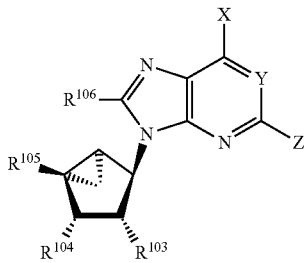

(II)

wherein: X is selected from NHR$^{101}$, CH$_3$, and CH=C(R$^a$)(R$^b$) wherein R$^a$ and R$^b$ are independently selected from hydrogen, hydroxyl, C$_1$-C$_6$ alkyl, and C$_6$-C$_{14}$ aryl;
Y is N or CH;
R$^{101}$ is selected from C$_1$-C$_6$ alkyl, C$_1$-C$_6$ alkoxy, hydroxyl, C$_3$-C$_8$ cycloalkyl, C$_6$-C$_{14}$ aryl C$_3$-C$_8$ cycloalkyl, C$_3$-C$_8$ cycloalkyl C$_1$-C$_6$ alkyl, C$_3$-C$_8$ dicycloalkyl C$_1$-C$_6$ alkyl, C$_7$-C$_{12}$ bicycloalkyl, C$_7$-C$_{12}$ bicycloalkyl C$_1$-C$_6$ alkyl, C$_7$-C$_{14}$ tricycloalkyl C$_1$-C$_6$ alkyl, C$_6$-C$_{14}$ aryl, C$_6$-C$_{14}$ aryl C$_1$-C$_6$ alkyl, C$_6$-C$_{14}$ diaryl C$_1$-C$_6$ alkyl, C$_6$-C$_{14}$ aryl C$_1$-C$_6$ alkoxy, heterocyclyl C$_1$-C$_6$ alkyl, heterocyclyl, 4-[[[4-[[[(2-amino C$_1$-C$_6$ alkyl)amino]-carbonyl]-C$_1$-C$_6$ alkyl]anilino]carbonyl]C$_1$-C$_6$ alkyl]C$_6$-C$_{14}$ aryl, and C$_6$-C$_{14}$ aryl C$_3$-C$_8$ cycloalkyl, wherein the aryl or heterocyclyl portion of R$^{101}$ is optionally substituted with one or more substituents selected from halo, amino, hydroxyl, carboxy, alkoxycarbonyl, aminocarbonyl, alkylaminocarbonyl, dialkylaminocarbonyl, C$_1$-C$_6$ alkyl, C$_2$-C$_6$ alkenyl, C$_2$-C$_6$ alkynyl, C$_1$-C$_6$ alkoxy, C$_6$-C$_{14}$ aryloxy, hydroxy C$_1$-C$_6$ alkyl, hydroxy C$_2$-C$_6$ alkenyl, hydroxy C$_2$-C$_6$ alkynyl, carboxy C$_1$-C$_6$ alkyl, carboxy C$_2$-C$_6$ alkenyl, carboxy C$_2$-C$_6$ alkynyl, aminocarbonyl C$_1$-C$_6$ alkyl, aminocarbonyl C$_2$-C$_6$ alkenyl, aminocarbonyl C$_2$-C$_6$ alkynyl, and any combination thereof; and the alkyl or cycloalkyl portion of R$^{101}$ is optionally substituted with one or more substituents selected from halo, amino, alkyl, alkoxy, aryloxy, hydroxyalkyl, hydroxyalkenyl, hydroxyalkynyl, aminocarbonylalkoxy, and arylalkoxy, and any combination thereof;
Z is halo, azido, or a group of the formula:

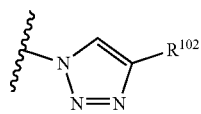

wherein R$^{102}$ is selected from C$_6$-C$_{12}$ aryl, C$_6$-C$_{12}$ aryl-C$_1$-C$_6$ alkyl, C$_3$-C$_8$ cycloalkyl, heteroaryl, and metallocenyl, wherein the aryl group is optionally substituted with one or more substituents selected from trifluoromethyl, hydroxyalkyl, alkoxy, sulfonyloxy, carboxyalkyl, sulfonyloxyalkyl, arylcarbonyl, and any combination thereof, wherein the heteroaryl group is optionally substituted with one or more substituents selected from halo, trifluoromethyl, amino, alkyl, hydroxyalkyl, aryl, alkoxy, hydroxyl, carboxyl, sulfonyloxy, carboxyalkyl, sulfonyloxyalkyl, alkylcarbonyl, arylcarbonyl, and any combination thereof,
R$^{103}$ and R$^{104}$ are independently selected from hydrogen, hydroxyl, amino, mercapto, ureido, C$_1$-C$_6$ alkyl carbonylamino, hydroxy C$_1$-C$_6$ alkyl, and hydrazinyl R$^{105}$ is selected from hydrogen, $C_1$-$C_3$ alkyl aminocarbonyl, di($C_1$-$C_3$ alkyl) aminocarbonyl, $C_1$-$C_3$ alkylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl; and $R^{106}$ is selected from hydrogen, $C_1$-$C_6$ alkyl, $C_2$-$C_6$ alkenyl, $C_2$-$C_6$ alkynyl, heteroaryl, and $C_1$-$C_6$ aminoalkyl;

or a pharmaceutically acceptable salt thereof, with the proviso that, when $R^{103}$ and $R^{104}$ are both hydroxyl, $R^{105}$ is methylaminocarbonyl, $R^{106}$ is hydrogen, X is NHMe, and Y is CH, then Z is not iodo.

In certain embodiment for a compound of formula (II), $R^{106}$ is hydrogen.

In certain embodiment for a compound of formula (II), Y is N.

In certain embodiment for a compound of formula (II), $R^{105}$ is selected from $C_1$-$C_3$ alkyl aminocarbonyl or di($C_1$-$C_3$ alkyl) aminocarbonyl.

In certain embodiment for a compound of formula (II), $R^{103}$ and $R^{104}$ are both hydroxyl.

In certain embodiment for a compound of formula (II), X is $NHR^{101}$. In a preferred embodiment, $R^{101}$ is $C_1$-$C_6$ alkyl.

In certain embodiment for a compound of formula (II), Z is

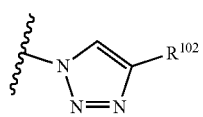

In certain embodiment for a compound of formula (II), $R^{102}$ is $C_6$-$C_{10}$ aryl, wherein the aryl group is substituted with one or more substituents selected from trifluoromethyl, hydroxyalkyl, alkoxy, and any combination thereof.

In certain embodiment for a compound of formula (II), $R^{102}$ is heteroaryl, and the heteroaryl group is optionally substituted with one or more substituents selected from halo, hydroxy, and alkyl.

In certain preferred embodiments, the compound is selected from:

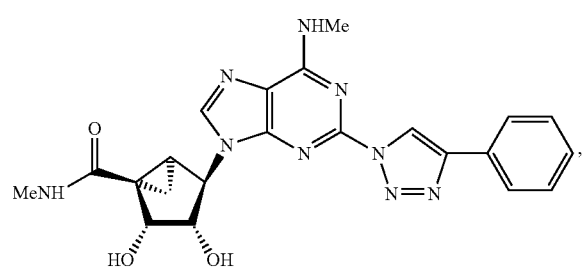

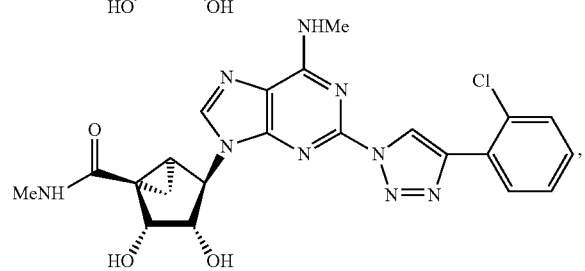

-continued

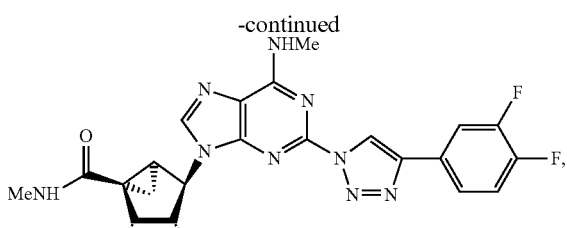

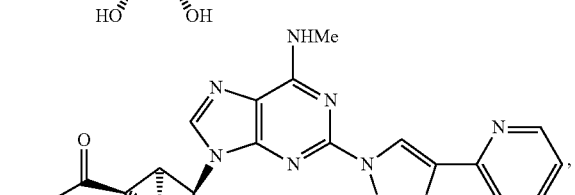

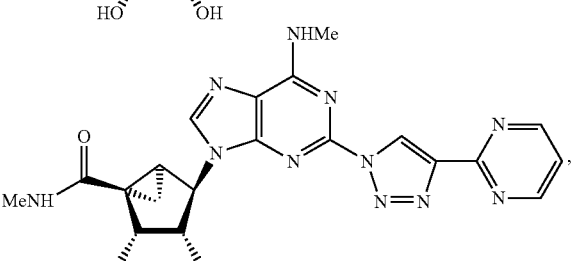

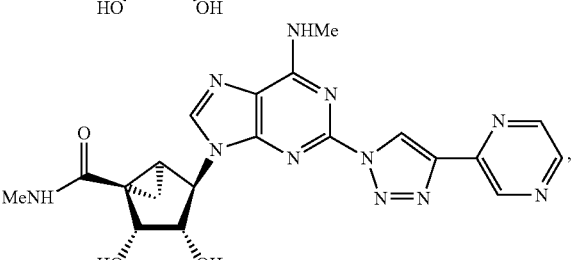

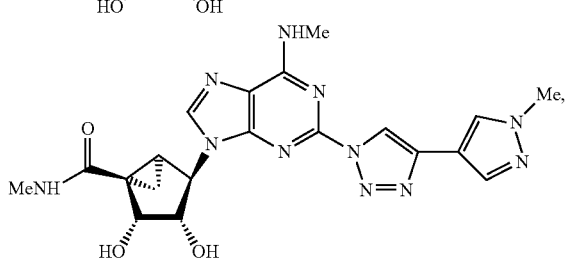

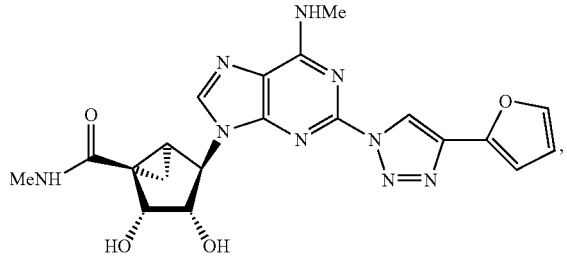

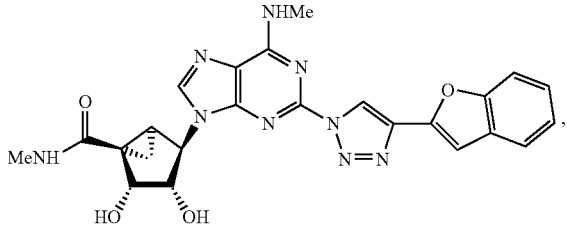

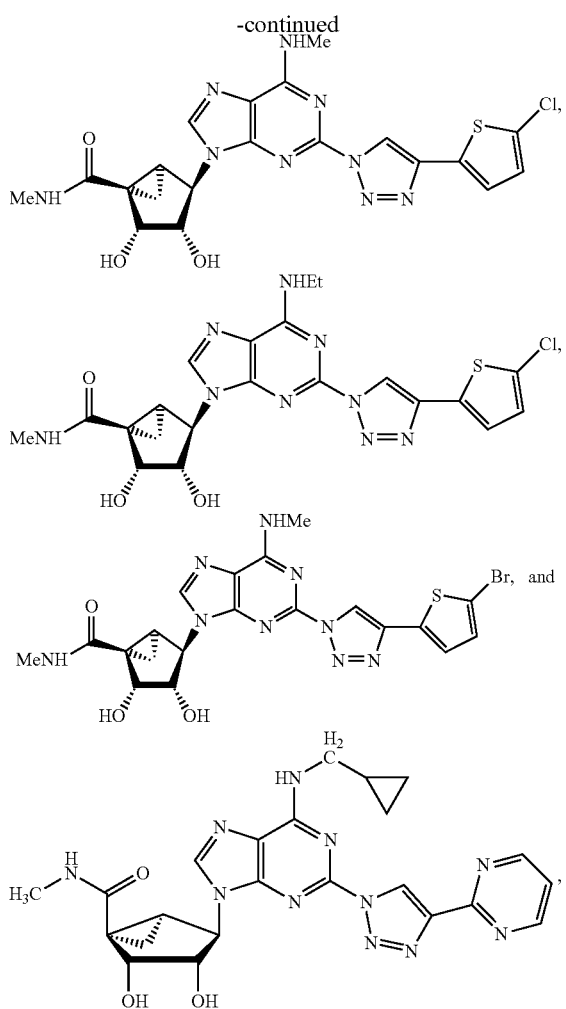

and a salt of any one thereof.

According to one embodiment, the therapeutically effective amount is from 0.1 mg to 1.0 gram per day per patient (nominally weighing 60 kilograms) or equivalent amounts calculated on the basis of milligrams per kilogram of body weight, or on the basis of milligram per meter-squared of body surface area. The appropriate dosage can vary depending on the mode of administration, the particular condition to be treated and the effect desired.

Suitable subjects include non-human animals, such as, for example, nematodes, mammals, non-human primates, rodents (e.g., mice, rats, and hamsters), stock and domesticated animals (e.g., pigs, cows, sheep, horses, cats, and dogs), and birds. Particularly suitable subjects include humans. As used herein, "subject in need thereof" (also used interchangeably herein with "a patient in need thereof" and "an individual in need thereof") refers to a subject susceptible to or at risk of a specified disease, disorder, or condition. More particularly, in the present disclosure the methods of can be used with an individual or subset of individuals who have, are susceptible to, and at elevated risk for experiencing migraine, migraine-like headaches such as post-traumatic headache, and other related headaches, such as TACs. The methods can also be used with an individual or subset of individuals who have, are susceptible to, and at elevated risk for experiencing migraine, migraine-like headaches such as post-traumatic headache, and other related headaches. Individuals may be susceptible to or at elevated risk for these disorders or conditions due to family history, age, environment, and/or lifestyle. As used herein, "susceptible" and "at risk" refer to having little resistance to a certain disease, disorder or condition, including being genetically predisposed, having a family history of, and/or having symptoms of the disease, disorder or condition. Based on the foregoing, because some of the method embodiments of the present disclosure are directed to specific subsets or subclasses of identified subjects (that is, the subset or subclass of subjects "in need" of assistance in addressing one or more specific conditions noted herein), not all subjects will fall within the subset or subclass of subjects as described herein for certain diseases, disorders or conditions.

The effective amount may be given via any standard drug administration method, including but not limited to injections via the intravenous, intramuscular, subcutaneous, and intrathecal routes; via inhalation (nasal or oral); per os; per rectum; or via transcutaneous methods (patches, ointments, salves, etc.).

The A3AR agonist may be formulated according to any generally known pharmaceutical method (Remington & Gennaro, 2015) that is appropriate for the intended route of administration, including any generally known and appropriate vehicle, salt or hydrate, or in any appropriate molecular precursor form (i.e., pro-drug). According to another embodiment, the A3AR agonist is formulated in a manner intended to promote transfer across the blood-brain-barrier via any method known to one skilled in the art. The A3AR agonist of the present disclosure can be administered to animals, preferably to mammals, and in particular to humans as therapeutics per se, as mixtures with one another or in the form of pharmaceutical preparations, and which as active constituent contains an effective dose of the compositions, in addition to customary pharmaceutically innocuous excipients and additives. The active ingredients can be introduced in a pharmaceutical composition together with one or more adjuvants, excipients, carriers, buffers, diluents, and/or other customary pharmaceutical auxiliaries. Pharmaceutically acceptable carriers, and, optionally, other therapeutic and/or prophylactic ingredients must be "acceptable" in the sense of being compatible with the other ingredients of the formulation and not harmful to the recipient thereof.

According to one embodiment, the A3AR agonist may be given on a daily basis (once, twice, three times or 4 times per day) to a patient diagnosed with any subtype of migraine, migraine-like headaches such as post-traumatic headache, and other related headaches.

All of the compositions and/or methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and/or methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

REFERENCES

The following references, to the extent that they provide exemplary procedural or other details supplementary to those set forth herein, are specifically incorporated herein by reference:

Remington J P & Gennaro A R. *Remington: The Science and Practice of Pharmacy,* 2015, 22nd Edition, Mack Co., Easton PA.

Tosh D K, et al. In vivo phenotypic screening for treating chronic neuropathic pain: modification of C2-arylethynyl group of conformationally constrained A3 adenosine receptor agonists. *Journal Medicinal Chemistry* (2014) 57: 9901-14.

Tosh D K, et al. Efficient, large-scale synthesis and preclinical studies of MRS5698, a highly selective A3 adenosine receptor agonist that protects against chronic neuropathic pain. *Purinergic Signalling* (2015a) 11:371-387.

Tosh D K, et al. Structure-based design, synthesis by click chemistry and in vivo activity of highly selective A3 adenosine receptor agonists. *Medicinal Chemistry Communications* (2015b) 6: 555-63.

Tosh D K, et al. Rigidified A3 adenosine receptor agonists: 1-deazaadenine modification maintains high in vivo efficacy. *ACS Medicinal Chemistry Letters* (2015c) 6: 804-8.

Tosh D K, et al. Purine (N)-methanocarba nucleoside derivatives lacking an exocyclic amine as selective A3 adenosine receptor agonists. *Journal Medicinal Chemistry* (2016) 59: 3249-63.

What is claimed is:

1. A method for the treatment of migraine, trigeminal autonomic cephalalgias, medication overuse headache, or post-traumatic headache, the method comprising: administering a selective agonist for the human adenosine A3 receptor (A3 AR) subtype to a patient in need thereof, wherein the selective agonist for the human adenosine A3 receptor subtype is a compound of Formula (I):

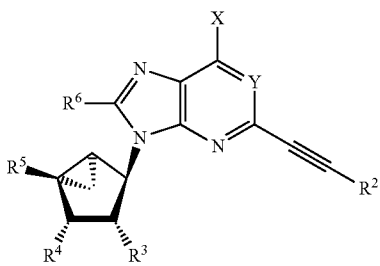

(I)

wherein:

X is selected from $NHR^1$, $CH_3$, and $CH=C(R^a)(R^b)$ wherein $R^a$ and $R^b$ are independently selected from hydrogen, hydroxyl, $C_1$-$C_6$ alkyl, and $C_6$-$C_{14}$ aryl;

Y is N or CH;

$R^1$ is selected from $C_1$-$C_6$ alkyl, $C_1$-$C_6$ alkoxy, hydroxyl, $C_3$-$C_8$ cycloalkyl, $C_6$-$C_{14}$ aryl $C_3$-$C_8$ cycloalkyl, $C_3$-$C_8$ cycloalkyl $C_1$-$C_6$ alkyl, $C_3$-$C_8$ dicycloalkyl $C_1$-$C_6$ alkyl, $C_7$-$C_{12}$ bicycloalkyl, $C_7$-$C_{12}$ bicycloalkyl $C_1$-$C_6$ alkyl, $C_7$-$C_{14}$ tricycloalkyl $C_1$-$C_6$ alkyl, $C_6$-$C_{14}$ aryl, $C_6$-$C_{14}$ aryl $C_1$-$C_6$ alkyl, $C_6$-$C_{14}$ diaryl $C_1$-$C_6$ alkyl, $C_6$-$C_{14}$ aryl $C_1$-$C_6$ alkoxy, heterocyclyl $C_1$-$C_6$ alkyl, heterocyclyl, 4-[[[4-[[[(2-amino $C_1$-$C_6$ alkyl) amino]-carbonyl]-$C_1$-$C_6$ alkyl]anilino]carbonyl]$C_1$-$C_6$ alkyl] $C_6$-$C_{14}$ aryl, and $C_6$-$C_{14}$ aryl $C_3$-$C_8$ cycloalkyl, wherein the aryl or heterocyclyl portion of $R^1$ is optionally substituted with one or more substituents selected from halo, amino, hydroxyl, carboxy, alkoxycarbonyl, aminocarbonyl, alkylaminocarbonyl, dialkylaminocarbonyl, $C_1$-$C_6$ alkyl, $C_2$-$C_6$ alkenyl, $C_2$-$C_6$ alkynyl, $C_1$-$C_6$ alkoxy, $C_6$-$C_{14}$ aryloxy, hydroxy $C_1$-$C_6$ alkyl, hydroxy $C_2$-$C_6$ alkenyl, hydroxy $C_2$-$C_6$ alkynyl, carboxy $C_1$-$C_6$ alkyl, carboxy $C_2$-$C_6$ alkenyl, carboxy $C_2$-$C_6$ alkynyl, aminocarbonyl $C_1$-$C_6$ alkyl, aminocarbonyl $C_2$-$C_6$ alkenyl, aminocarbonyl $C_2$-$C_6$ alkynyl, and any combination thereof; and the alkyl or cycloalkyl portion of $R^1$ is optionally substituted with one or more substituents selected from halo, amino, alkyl, alkoxy, aryloxy, hydroxyalkyl, hydroxyalkenyl, hydroxyalkynyl, aminocarbonylalkoxy, and arylalkoxy, and any combination thereof;

$R^2$ is selected from $C_6$-$C_{12}$ aryl, $C_3$-$C_8$ cycloalkyl, heteroaryl, and metallocenyl, wherein the aryl group is substituted with one or more substituents selected from trifluoromethyl, hydroxyalkyl, alkoxy, sulfonyloxy, carboxyalkyl, sulfonyloxyalkyl, arylcarbonyl, and any combination thereof, wherein the heteroaryl group is optionally substituted with one or more substituents selected from halo, trifluoromethyl, amino, alkyl, hydroxyalkyl, aryl, benzo, alkoxy, hydroxyl, carboxyl, sulfonyloxy, carboxyalkyl, sulfonyloxyalkyl, alkylcarbonyl, arylcarbonyl, and any combination thereof;

$R^3$ and $R^4$ are independently selected from hydrogen, hydroxyl, amino, mercapto, ureido, $C_1$-$C_6$ alkyl carbonylamino, hydroxy $C_1$-$C_6$ alkyl, and hydrazinyl;

$R^5$ is selected from $C_1$-$C_3$ alkyl aminocarbonyl, di($C_1$-$C_3$ alkyl) aminocarbonyl, $C_1$-$C_3$ alkylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxylamino, and $C_2$-$C_3$ alkenyl; and $R^6$ is selected from hydrogen, $C_1$-$C_6$ alkyl, $C_2$-$C_6$ alkenyl, $C_2$-$C_6$ alkynyl, heteroaryl, and $C_1$-$C_6$ aminoalkyl;

or a pharmaceutically acceptable salt thereof.

2. The method of claim 1, wherein when $R^1$ is methyl, $R^3$ and $R^4$ are both hydroxyl, $R^6$ is hydrogen, and $R^5$ is methylaminocarbonyl, $R^2$ is not 2-pyridyl or phenyl.

3. The method of claim 1, when $R^1$ is methyl, $R^3$ and $R^4$ are both hydroxyl, $R^6$ is hydrogen, and $R^5$ is methylaminocarbonyl, $R^2$ is not 2-pyridyl.

4. The method of claim 1, wherein $R^6$ is hydrogen.

5. The method of claim 1, wherein Y is N.

6. The method of claim 1, wherein $R^5$ is selected from $C_1$-$C_3$ alkyl aminocarbonyl or di($C_1$-$C_3$ alkyl)aminocarbonyl.

7. The method of claim 1, $R^3$ and $R^4$ are both hydroxyl.

8. The method of claim 1, wherein X is $NHR^1$ and $R^1$ is $C_1$-$C_6$ alkyl.

9. The method of claim 1, wherein $R^2$ is $C_6$-$C_{10}$ aryl, wherein the aryl group is substituted with one or more substituents independently selected from halo, trifluoromethyl, hydroxyalkyl, and alkoxy.

10. The method of claim 1, wherein $R^2$ is heteroaryl, and the heteroaryl group is optionally substituted with one or more substituents independently selected from hydroxy, halo and alkyl.

11. The method of claim 1, wherein the compound is selected from:

21
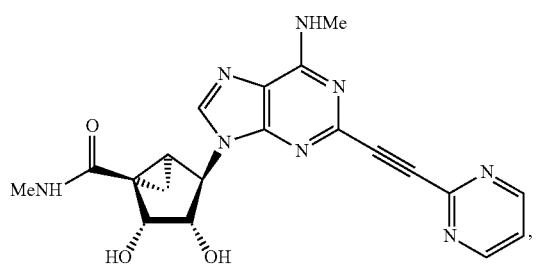
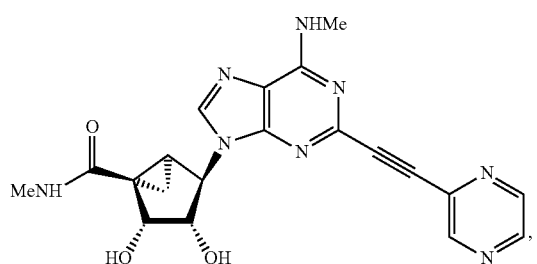
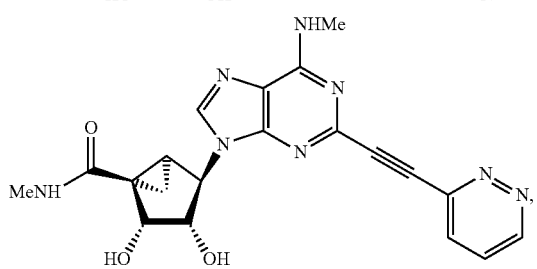
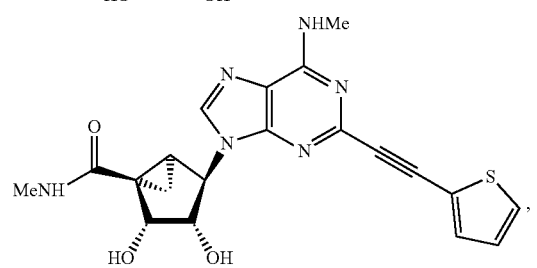
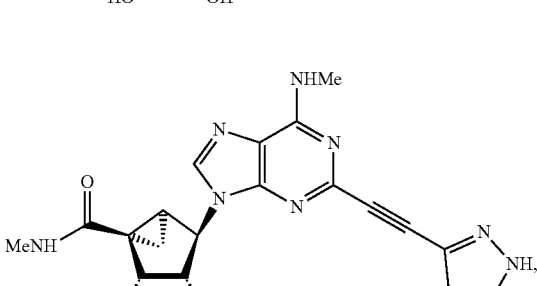
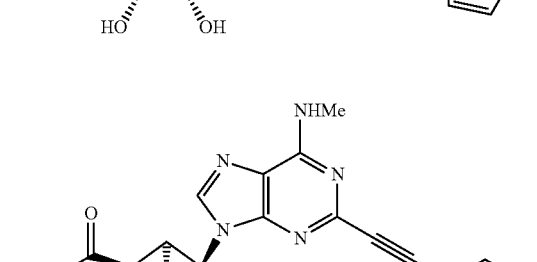
22
-continued
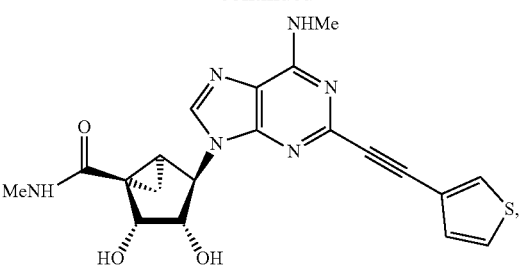
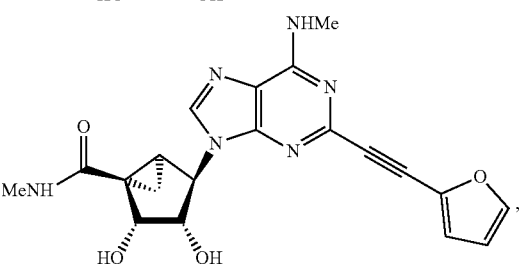
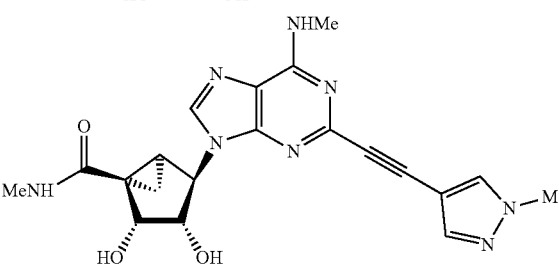
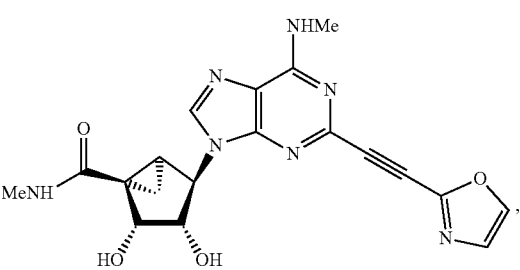
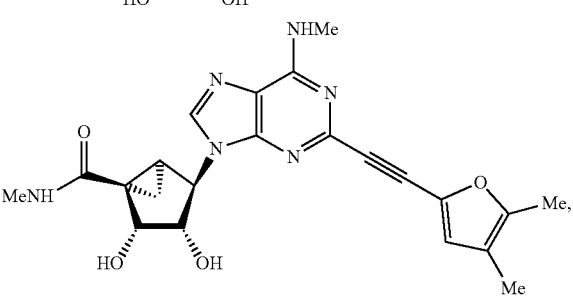
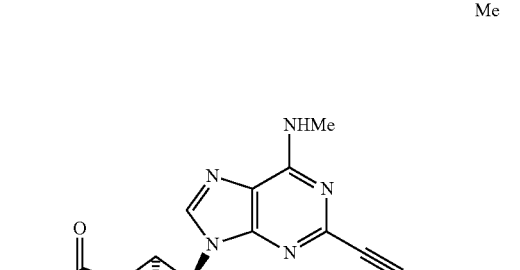

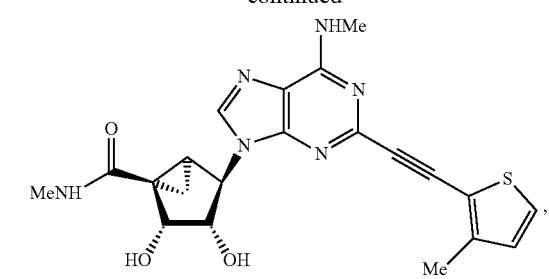
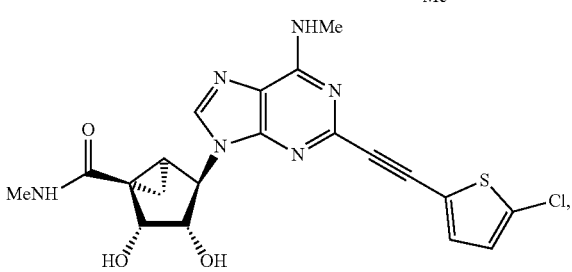
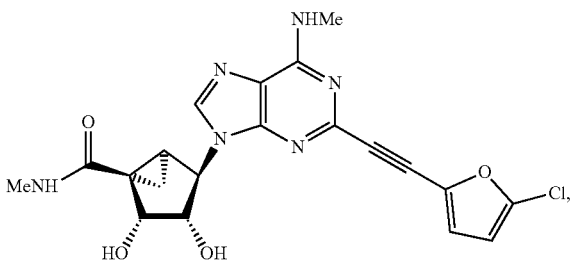
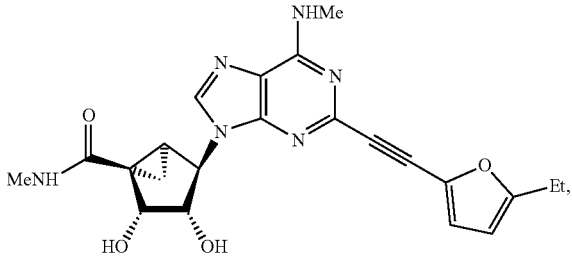
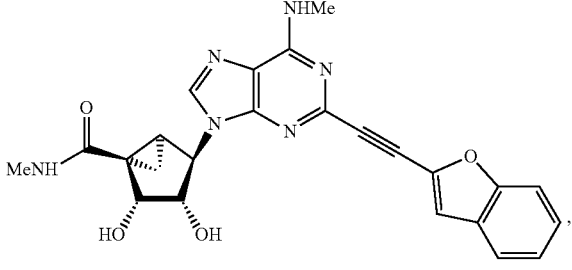
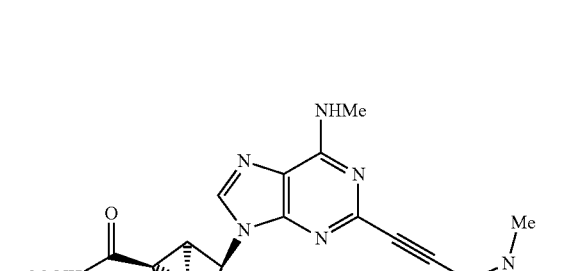
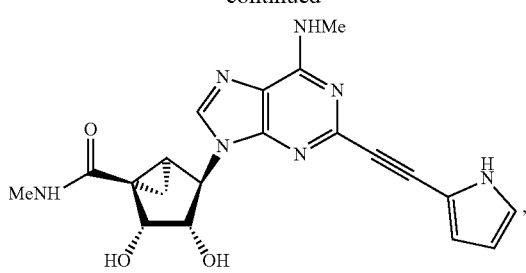
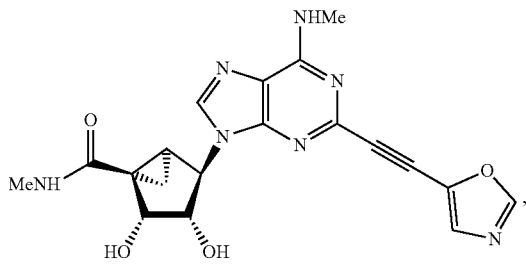
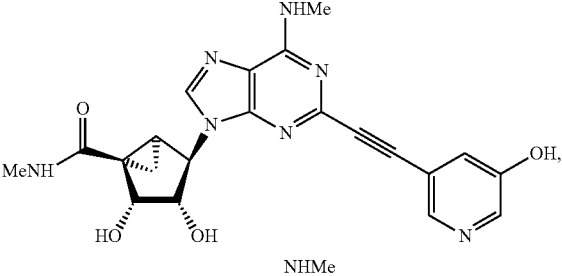
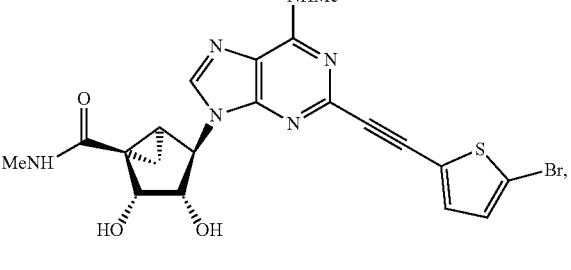
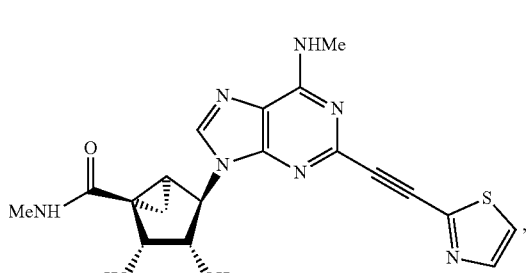
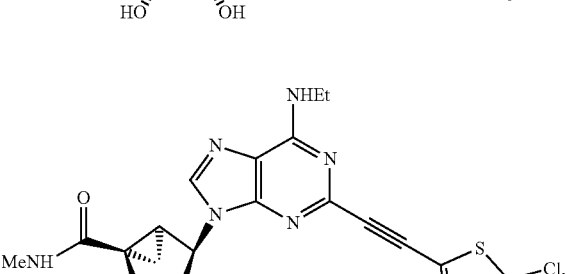

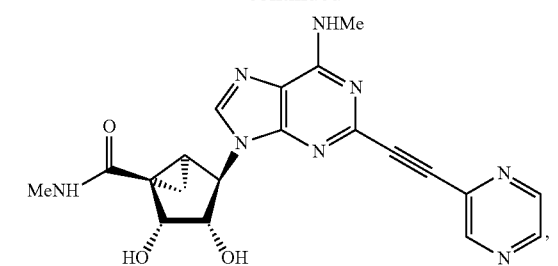
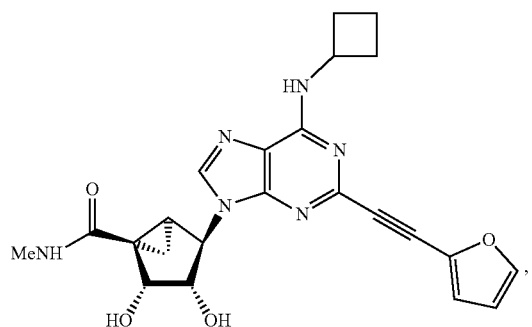
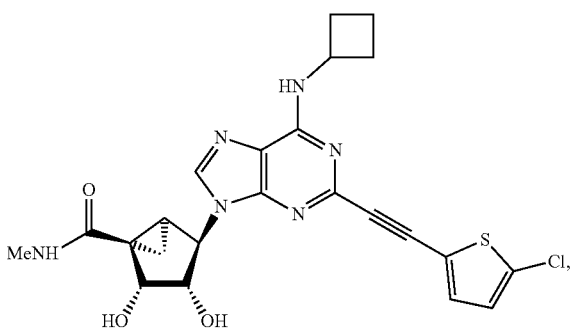
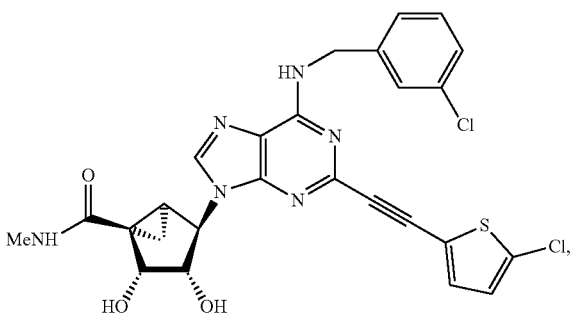
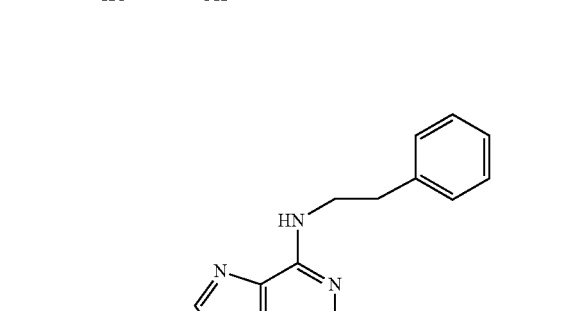
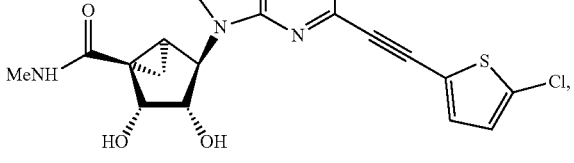
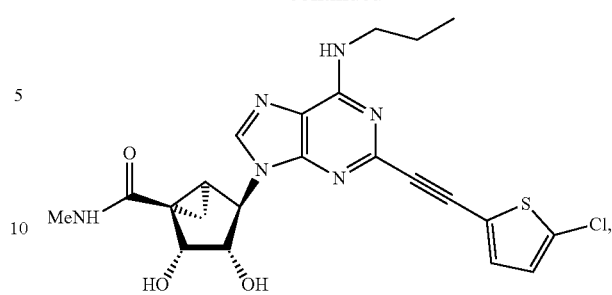
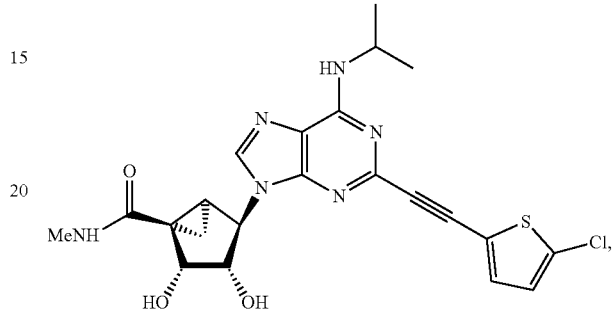
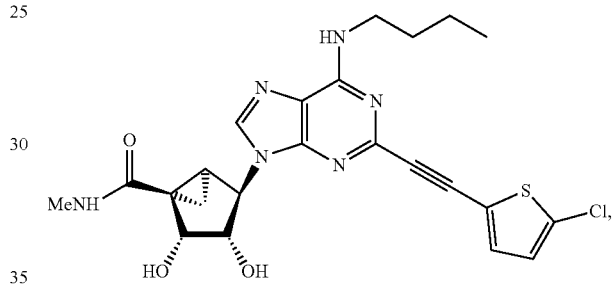
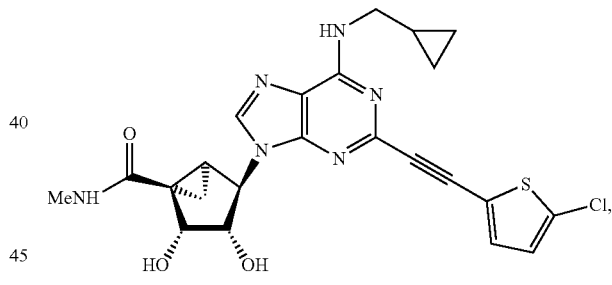
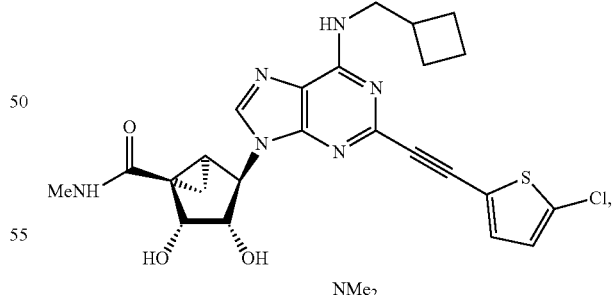
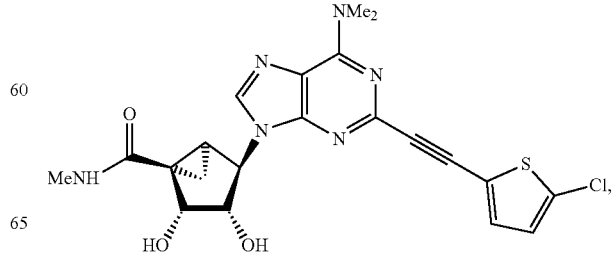

-continued

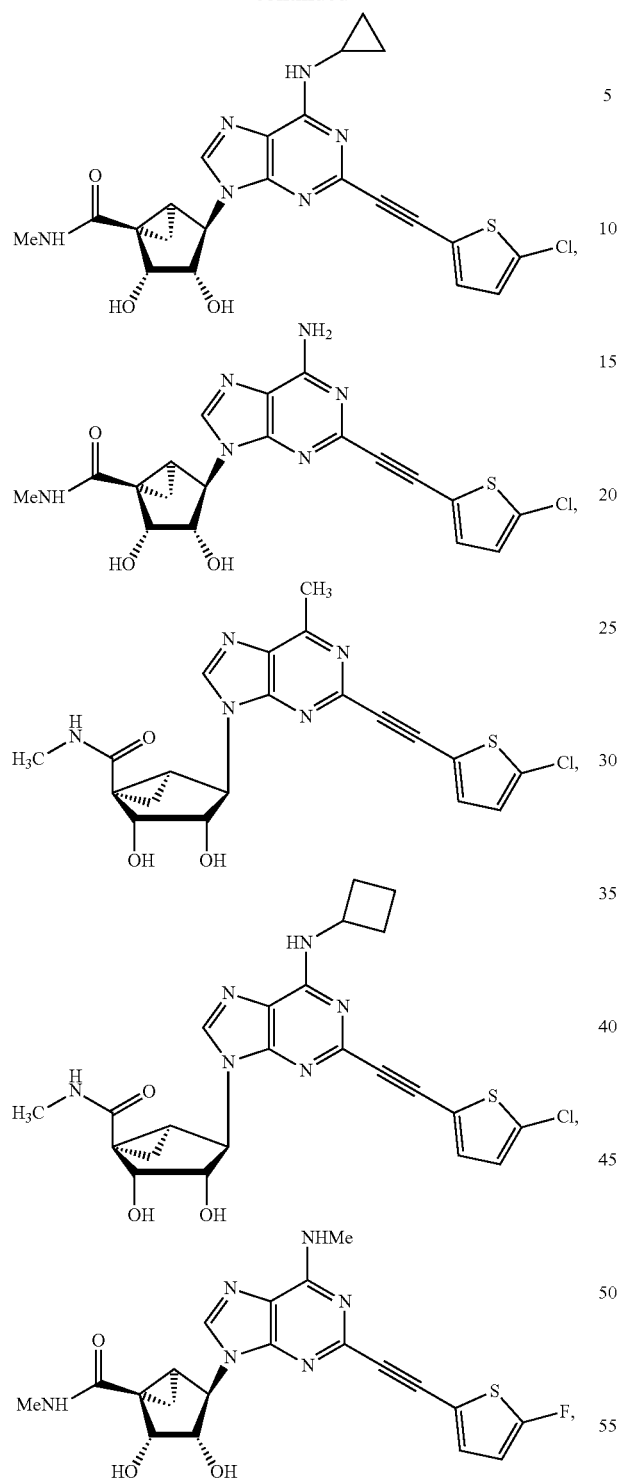

salt of any one thereof.

12. The method of claim 1, wherein the selective agonist for the adenosine A3 human receptor subtype is a compound of Formula (II):

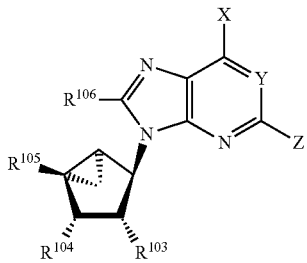

(II)

wherein:

X is selected from NHR$^{101}$, CH$_3$, and CH=C(R$^a$)(R$^b$) wherein R$^a$ and R$^b$ are independently selected from hydrogen, hydroxyl, C$_1$-C$_6$ alkyl, and C$_6$-C$_{14}$ aryl;

Y is N or CH;

R$^{101}$ is selected from C$_1$-C$_6$ alkyl, C$_1$-C$_6$ alkoxy, hydroxyl, C$_3$-C$_8$ cycloalkyl, C$_6$-C$_{14}$ aryl C$_3$-C$_8$ cycloalkyl, C$_3$-C$_8$ cycloalkyl C$_1$-C$_6$ alkyl, C$_3$-C$_8$ dicycloalkyl C$_1$-C$_6$ alkyl, C$_7$-C$_{12}$ bicycloalkyl, C$_7$-C$_{12}$ bicycloalkyl C$_1$-C$_6$ alkyl, C$_7$-C$_{14}$ tricycloalkyl C$_1$-C$_6$ alkyl, C$_6$-C$_{14}$ aryl, C$_6$-C$_{14}$ aryl C$_1$-C$_6$ alkyl, C$_6$-C$_{14}$ diaryl C$_1$-C$_6$ alkyl, C$_6$-C$_{14}$ aryl C$_1$-C$_6$ alkoxy, heterocyclyl C$_1$-C$_6$ alkyl, heterocyclyl, 4-[[[4-[[[(2-amino C$_1$-C$_6$ alkyl)amino]-carbonyl]-C$_1$-C$_6$ alkyl]anilino]carbonyl]C$_1$-C$_6$ alkyl]C$_6$-C$_{14}$ aryl, and C$_6$-C$_{14}$ aryl C$_3$-C$_8$ cycloalkyl, wherein the aryl or heterocyclyl portion of R$^{101}$ is optionally substituted with one or more substituents selected from halo, amino, hydroxyl, carboxy, alkoxycarbonyl, aminocarbonyl, alkylaminocarbonyl, dialkylaminocarbonyl, C$_1$-C$_6$ alkyl, C$_2$-C$_6$ alkenyl, C$_2$-C$_6$ alkynyl, C$_1$-C$_6$ alkoxy, C$_6$-C$_{14}$ aryloxy, hydroxy C$_1$-C$_6$ alkyl, hydroxy C$_2$-C$_6$ alkenyl, hydroxy C$_2$-C$_6$ alkynyl, carboxy C$_1$-C$_6$ alkyl, carboxy C$_2$-C$_6$ alkenyl, carboxy C$_2$-C$_6$ alkynyl, aminocarbonyl C$_1$-C$_6$ alkyl, aminocarbonyl C$_2$-C$_6$ alkenyl, aminocarbonyl C$_2$-C$_6$ alkynyl, and any combination thereof; and the alkyl or cycloalkyl portion of R$^{101}$ is optionally substituted with one or more substituents selected from halo, amino, alkyl, alkoxy, aryloxy, hydroxyalkyl, hydroxyalkenyl, hydroxyalkynyl, aminocarbonylalkoxy, and arylalkoxy, and any combination thereof;

Z is halo, azido, or a group of the formula:

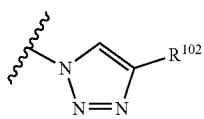

wherein R$^{102}$ is selected from C$_6$-C$_{12}$ aryl, C$_6$-C$_{12}$ aryl-C$_1$-C$_6$ alkyl, C$_3$-C$_8$ cycloalkyl, heteroaryl, and metallocenyl, wherein the aryl group is optionally substituted with one or more substituents selected from trifluoromethyl, hydroxyalkyl, alkoxy, sulfonyloxy, carboxyalkyl, sulfonyloxyalkyl, arylcarbonyl, and any combination thereof, wherein the heteroaryl group is optionally substituted with one or more substituents selected from halo, trifluoromethyl, amino, alkyl, hydroxyalkyl, aryl, alkoxy, hydroxyl, carboxyl, sulfonyloxy, carboxyalkyl, sulfonyloxyalkyl, alkylcarbonyl, arylcarbonyl, and any combination thereof, R$^{103}$ and R$^{104}$ are independently selected from hydrogen, hydroxyl, amino, mercapto, ureido, C$_1$-C$_6$ alkyl carbonylamino, hydroxy C$_1$-C$_6$ alkyl, and hydrazinyl $R^{105}$ is selected from hydrogen, $C_1$-$C_3$ alkyl aminocarbonyl, di($C_1$-$C_3$ alkyl) aminocarbonyl, $C_1$-$C_3$ alkylthio $C_1$-$C_3$ alkyl, halo $C_1$-$C_3$ alkyl, hydrazinyl, amino $C_1$-$C_3$ alkyl, hydroxy $C_1$-$C_3$ alkyl, $C_3$-$C_6$ cycloalkylamino, hydroxyl amino, and $C_2$-$C_3$ alkenyl; and $R^{106}$ is selected from hydrogen, $C_1$-$C_6$ alkyl, $C_2$-$C_6$ alkenyl, $C_2$-$C_6$ alkynyl, heteroaryl, and $C_1$-$C_6$ aminoalkyl; or a pharmaceutically acceptable salt thereof, with the proviso that, when $R^{103}$ and $R^{104}$ are both hydroxyl, $R^{105}$ is methylaminocarbonyl, $R^{106}$ is hydrogen, X is NHMe, and Y is CH, then Z is not iodo.

13. The method of claim 12, wherein Y is N.
14. The method of claim 12, wherein $R^{103}$ and $R^{104}$ are both hydroxyl.
15. The method of claim 12, wherein X is $NHR^{101}$ and $R^{101}$ is $C_1$-$C_6$ alkyl.
16. The method of claim 12, wherein Z is

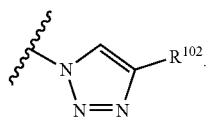

17. The method of claim 16, wherein $R^{102}$ is $C_6$-$C_{10}$ aryl, wherein the aryl group is substituted with one or more substituents independently selected from trifluoromethyl, hydroxyalkyl, alkoxy, and any combination thereof.
18. The method of claim 16, wherein $R^{102}$ is heteroaryl, and the heteroaryl group is optionally substituted with one or more substituents independently selected from halo, hydroxy, and alkyl.
19. The method of claim 12, wherein the compound is selected from:

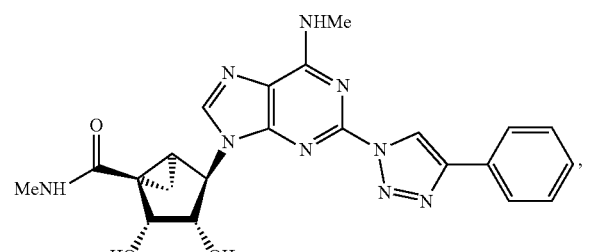

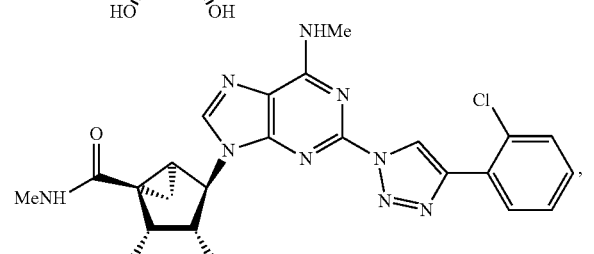

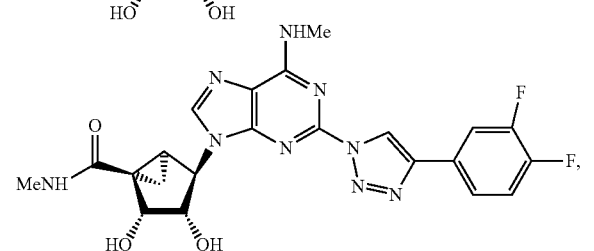

-continued

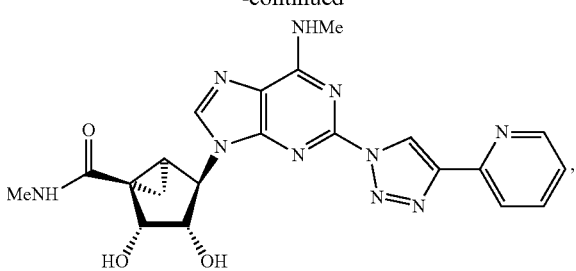

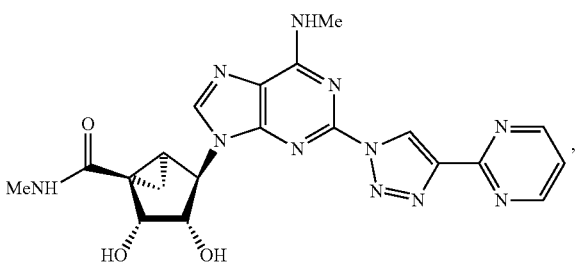

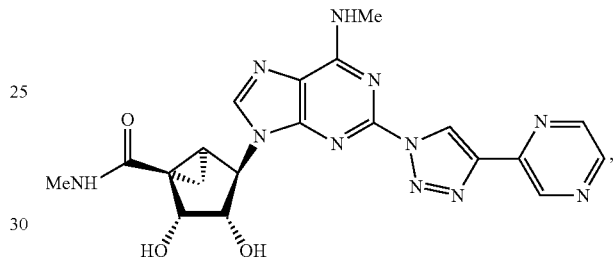

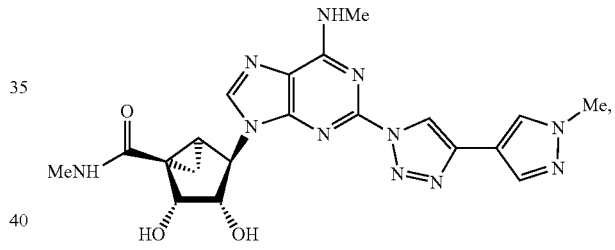

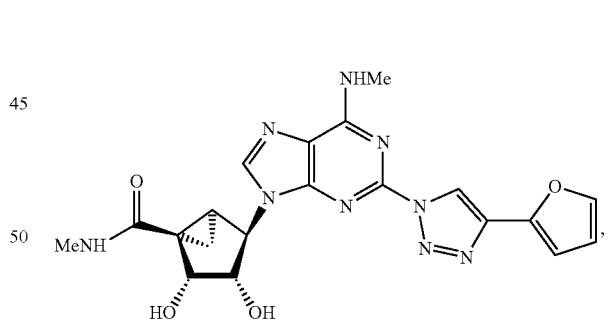

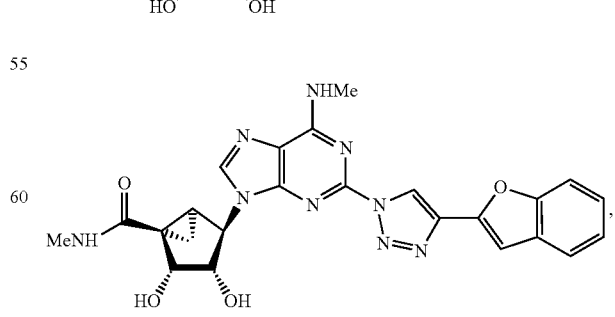

31
-continued
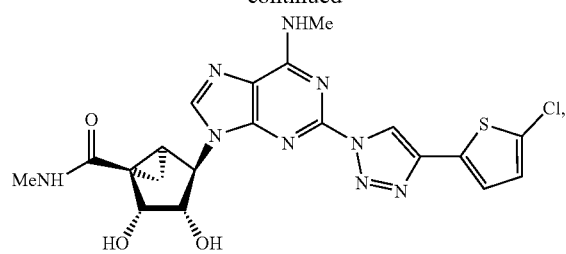
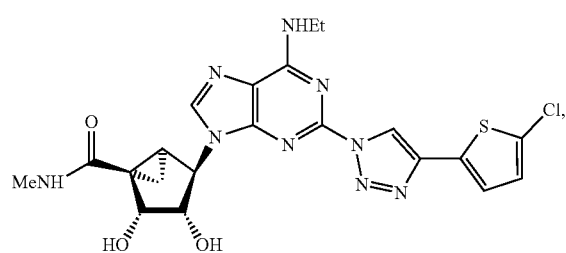
32
-continued
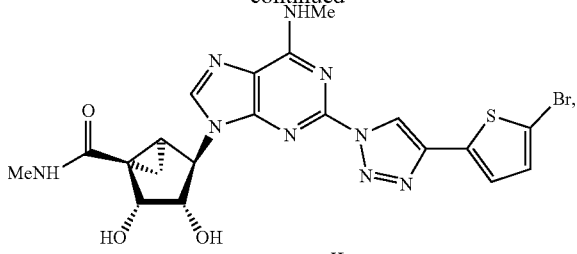
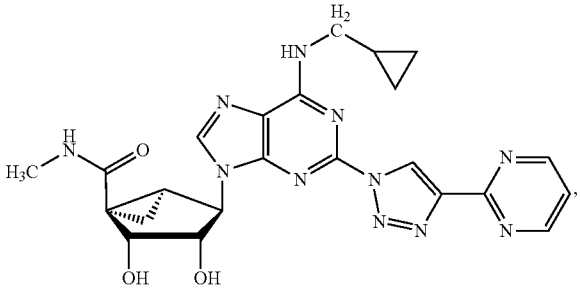
and a salt of any one thereof.
\* \* \* \* \*